(12) United States Patent
Ghouri

(10) Patent No.: US 8,032,394 B1
(45) Date of Patent: Oct. 4, 2011

(54) SYSTEM AND METHOD FOR A PATIENT-SPECIFIC AND OPTIMIZATION OF MEDICAL THERAPY BY SIMULTANEOUS SYMBOLIC REASONING IN ALL CLINICAL DIMENSIONS

(75) Inventor: Ahmed Ghouri, San Diego, CA (US)

(73) Assignee: Anvita, Inc., San Diego, CA (US)

( * ) Notice: Subject to any disclaimer, the term of this patent is extended or adjusted under 35 U.S.C. 154(b) by 148 days.

(21) Appl. No.: 12/267,338

(22) Filed: Nov. 7, 2008

Related U.S. Application Data

(62) Division of application No. 10/350,483, filed on Jan. 23, 2003, now Pat. No. 7,809,585.

(60) Provisional application No. 60/388,444, filed on Jun. 12, 2002, now abandoned.

(51) Int. Cl.
*G06Q 50/00* (2006.01)
(52) U.S. Cl. .................................. 705/2; 705/3
(58) Field of Classification Search .............. 705/2, 3; 704/9; 600/300
See application file for complete search history.

(56) References Cited

U.S. PATENT DOCUMENTS

| | | | |
|---|---|---|---|
| 4,839,822 A | | 6/1989 | Dormond et al. |
| 5,660,176 A | | 8/1997 | Iliff |
| 5,737,539 A | | 4/1998 | Edelson et al. |
| 5,833,599 A | | 11/1998 | Schrier et al. |
| 5,867,821 A | | 2/1999 | Ballantyne et al. |
| 6,000,828 A | | 12/1999 | Leet |
| 6,024,699 A | | 2/2000 | Surwit et al. |
| 6,081,786 A | * | 6/2000 | Barry et al. .................... 705/3 |
| 6,151,581 A | | 11/2000 | Kraftson et al. |
| 6,266,645 B1 | * | 7/2001 | Simpson ........................ 705/3 |
| 6,292,771 B1 | * | 9/2001 | Haug et al. ...................... 704/9 |
| 6,338,039 B1 | | 1/2002 | Lonski et al. |
| 6,421,650 B1 | | 7/2002 | Goetz et al. |
| 6,678,669 B2 | * | 1/2004 | Lapointe et al. ............... 706/15 |
| 6,915,254 B1 | * | 7/2005 | Heinze et al. .................. 704/9 |
| 7,124,031 B1 | | 10/2006 | Hoffman et al. |
| 2002/0010595 A1 | | 1/2002 | Kapp |
| 2002/0019749 A1 | | 2/2002 | Becker et al. |
| 2002/0026330 A1 | | 2/2002 | Klein |
| 2002/0029223 A1 | | 3/2002 | Rice et al. |
| 2002/0032582 A1 | | 3/2002 | Feeney et al. |
| 2002/0035484 A1 | | 3/2002 | McCormick |
| 2002/0040305 A1 | | 4/2002 | Nakatsuchi et al. |
| 2002/0052760 A1 | | 5/2002 | Munoz et al. |
| 2002/0091546 A1 | | 7/2002 | Christakis et al. |
| 2002/0095313 A1 | | 7/2002 | Haq |
| 2002/0116219 A1 | | 8/2002 | Ibok et al. |
| 2002/0143582 A1 | | 10/2002 | Neuman et al. |
| 2002/0147615 A1 | | 10/2002 | Doerr et al. |
| 2002/0188466 A1 | | 12/2002 | Barrette et al. |
| 2003/0167189 A1 | * | 9/2003 | Lutgen et al. .................... 705/3 |
| 2003/0212576 A1 | * | 11/2003 | Kim .................................. 705/2 |
| 2006/0122807 A1 | | 6/2006 | Wittkowsky |
| 2006/0271407 A1 | | 11/2006 | Rosenfeld et al. |

* cited by examiner

*Primary Examiner* — Gerald J. O'Connor
*Assistant Examiner* — Natalie Pass
(74) *Attorney, Agent, or Firm* — DLA Piper US (LLP)

(57) ABSTRACT

A particular system and methodology by which a drug or medical therapy regimen is defined for any particular patient in a manner that takes not only a drug or therapy's effectiveness into account, but also an entire spectrum of relevant clinical dimensions so as minimize the possibility of harmful interactions while simultaneously maximizing pharmacotherapy potential. Furthermore, as a consequence of its construction, no medically relevant rule can be overlooked by the reasoning system. The system and methodology utilizes a computerized dimensional indexing system implementing multiple databases and performs therapeutic determinations by symbolic structural reasoning with respect to database elemental indices.

8 Claims, 5 Drawing Sheets

```
[PMedHx]  Diabetes Melitus

Type I Insulin Dependent with Ophthalmic Imp
          Type II Non-Insulin Dependent with Ophthalmi
          Type I Insulin Dependent with Neurological Im
          Type II Non-Insulin Dependent with Neurologic
          .
          .
```

[PMedHx] → [Screening Guidelines]
[PMedHx] → [Drug Interactions]
[PMedHx] → [Condition Interactions]

[PSurgHx] → [Narrow DDx]
[PSurgHx] → [Condition Interaction]
[PSurgHx] → [Drug Interaction]

[FamHx] → [Screening Guidelines]
[FamHx] → [Narrow DDx]

[SocHx] → [Screening Guidelines]
[SocHx] → [Narrow DDx]

| [Meds] | Indication (Dx) | [Aller] | |
|---|---|---|---|
| MYOBLOC | ACHALASIA | GLIPIZIDE | 5 |
| ALBUTEROL | ASTHMA | | |
| MONISTAT | CYSTITIS | | |
| CELEXA | PANIC DISORDER | | |
| ATENOLOL | UNSTABLE ANGINA | | |

3 Mild
4 Moderate
5 Severe

[PMedHx]

| ACHALASIA |
|---|
| ASTHMA |
| CYSTITIS |
| PANIC DISORDER |
| UNSTABLE ANGINA |
| ZINC DEFICIENCY |

[PSurgHx]

| AXILLO-FEMORAL BYPASS |
|---|
| GASTRECTOMY |
| ORCHIECTOMY, PARTIAL |

[Meds] → [Narrow DDx]
[Meds] → [Screening Guidelines]
[Meds] → [Drug-Drug Interactions]
[Meds] → [Drug-Condition Interactions]
[Meds] → [Drug-Disease Interactions]

[Aller] → [Narrow DDx]
[Aller] → [Aller-Drug Interaction]

*FIG. 4*

[ROS] = Initial Screening
  Q1 = (....)
    A1 =
    A2 =
    A3 =
  Q2 = (....)
    A1 =
    A2 =
    A3 =
  .
  .
  .
  Qn = (....)
    A1 =
    A2 =
    A3 =

[ROS] → [Narrow DDx]
[ROS] → [Test for New DDx]
[ROS] → [Screen for Co-existing PMedHx]
[ROS] → [Screen for Co-existing Condition]
[ROS] → [Screen for Co-existing Meds]

*FIG. 5*

[VS] → [Age-Related Screening]
[VS] → [Gender-Related Screening]
[VS] → [Age-Related Therapy]
[VS] → [Narrow DDx]

[PE] → [Disease Probability]
[PE] → [DDx for Disease]
[PE] → [Management Guidelines]

*FIG. 6*

| Drug | Formulary? | Unit Price |
|---|---|---|
| Drug A | Yes | $4.75 |
| Drug B | Yes | $3.25 |
| Drug C | Yes | $5.25 |
| Drug D | No | $7.25 |
| Drug E | No | $5.25 |
| Drug F | No | $9.25 |
| Drug G | Yes | $5.75 |
| Drug H | Yes | $0.25 |
| Drug J | Yes | $2.75 |
| Drug K | Yes | $1.15 |
| Drug L | Yes | $4.75 |
| Drug M | No | $5.25 |
| Drug N | Yes | $6.15 |
| Drug O | Yes | $2.25 |
| Drug P | Yes | $3.85 |
| Drug Q | Yes | $3.45 |
| . | . | . |
| Drug X | No | $5.75 |
| Drug Y | Yes | $6.55 |
| Drug Z | No | $7.00 |

Undifferentiated/Unsorted

Sort Order

1. Safety
2. Efficacy
3. Formulary
4. Price

| Drug | Formulary? | Unit Price |
|---|---|---|
| No Contraindications | | |
| Drug S | Yes | $1.25 |
| Drug C | Yes | $5.25 |
| Drug Q * | Yes | $3.45 |
| Drug E * | No | $5.25 |
| Drug X | No | $5.75 |
| Drug Z | No | $7.00 |
| Relative Contraindications | | |
| Drug H | Yes | $0.25 |
| Drug B | Yes | $3.25 |
| Drug D | No | $7.25 |
| Drug F | No | $9.25 |
| Absolute Contraindications | | |
| Drug K | Yes | $1.15 |
| Drug O | Yes | $2.25 |
| Drug T | No | $0.25 |
| Drug M | No | $5.25 |

\* Drugs E and Q require dosage adjustment

*FIG. 7*

SYSTEM AND METHOD FOR A PATIENT-SPECIFIC AND OPTIMIZATION OF MEDICAL THERAPY BY SIMULTANEOUS SYMBOLIC REASONING IN ALL CLINICAL DIMENSIONS

CROSS-REFERENCE TO RELATED APPLICATIONS

This application claims priority under 35 USC 120 to U.S. patent application Ser. No. 10/350,483 filed on Jan. 23, 2003 and entitled System and Method for Creating and Maintaining an Internet-Based, Universally Accessible and Anonymous Patient Medical Home Page, and takes priority from U.S. provisional patent application entitled Computerized System and Method for Rapid Data Entry of Past Medical Diagnoses, Ser. No. 60/388,444, filed Jun. 12, 2002, and is further related to U.S. patent application entitled Computerized System And Method For Rapid Data Entry Of Past Medical Diagnoses filed on instant date herewith, both commonly owned with the present application, the entire contents of which are expressly incorporated herein by reference.

FIELD OF THE INVENTION

The present invention relates to systems and methods for electronic medical therapy determination and more particularly to a computerized system and method for informing drug therapy regimens optimized for efficacy and safety by evaluating multiple clinical dimensions.

BACKGROUND OF THE INVENTION

The effective and safe administration of pharmaceutical products to patients, particularly in the context of determining an appropriate drug therapy following any clinical diagnosis, has become an evermore complex and challenging task for the modern healthcare professional. In particular, as clinical diagnoses and medical treatment becomes more sophisticated, the number of patients and indeed the number of illnesses or clinical indications, becomes proportionately larger, particularly in the case of expanded aged population growth. Further, as clinical indications (e.g., genetic variability in treatment guidelines) become better understood, a growing number of drugs and/or pharmaceuticals is becoming available for treatment of increasingly specific medical conditions.

With an ever growing number of pharmaceuticals products becoming available, so too is there an ever increasing amount of information associated with each of these pharmaceuticals products. Physicians are becoming overwhelmed with information of the type that is often critical for appropriate patient care. Examples of such information forms include consensus guidelines for patients with particular diseases, guidelines for specific medications and diagnostic screening guidelines for particular diseases and demographics. Other informational-type examples include clinical data on possible interactions between particular drugs, interactions between drugs and particular diseases, cross-allergies between drugs, and a voluminous set of diagnostic possibilities (often described as differential diagnoses) which need to be considered when a patient is associated with a lab test abnormality, physical finding, or particular complaint. Lack of mastery of these types of information, at the point of care, can lead to lethal or irreversible negative consequences to patient health or recovery prognosis.

Contemporary physicians are often presented with a choice between two less than optimal options; firstly, to attempt to memorize sufficient amounts of this type of information or, secondly, by referring to technical references (paper or electronic) as the need arises. These options are less than optimal in that memorization of all required information to practice state-of-the-art healthcare is formidable, if not impossible, for an ordinary human being. Further, exhaustive reference searches for specifically-needed information is not practical, given the average amount of time a physician is able to expend on any one particular patient. With regard to informational reference searches, the information must be actively sought after and is not generally found in any one particular reference set. References might include medical textbooks, journal articles, and other scientific publications, but might also include bulletins and notices periodically published by the various pharmaceuticals companies themselves, the U.S. Food and Drug Administration, insurance companies, and other similar entities. The physician must not only know what to look for, but also know where to look.

The above noted deficiencies in clinical information acquisition and publication is particularly troublesome in the development of appropriate drug therapy regimens. Developing an appropriate drug therapy, following any diagnosis, is an extremely complicated task and requires a physician to simultaneously consider the interaction characteristics of a large number of relevant clinical factors (termed herein as patient dimensions). In the current state of the art, a limited number of relatively crude, clinically incomplete decision support systems currently exist. These are generally classified as either drug interaction checkers or drug-metabolism impairment checkers.

For example, in the case of a drug-drug interaction checker, the decision support systems conventionally utilize a table of pre-defined possible drug-drug interactions and enable a physician to enter two or more drugs, in order to see if an interaction is expected within the parameters of the system. Drug X and drug Y, when used together, can cause undesirable side effects. However, drug X may have no interaction with drug Y, but drug X might cause serious harm if a patient has a co-existing disease Z. Thus, drug-drug interaction checkers are unable to make any determination with regard to a drug-disease interaction. For example, the heartburn drug Propulsid™ was withdrawn from the market because it was found to be potentially fatal when used in patients with a heart rhythm abnormality known as prolonged QT Syndrome. A simple drug-drug interaction checker would be unable to provide an alert to a physician on the basis of a drug-disease interaction. Importantly, interaction checking alone is not sufficient decision support for today's modern physician, because from the doctor's perspective, interaction warnings represent only potential problems, not potential solutions. As an example of this limitation, consider the MD who wishes to find which antibiotics are considered the most efficacious, in a specific geographical region, to treat a pneumonia caused by a specific strain of bacterium. Clearly an interaction checker alone is insufficient for the purposes of answering this question.

Drug metabolism impairment checkers represent another single-dimension decision support system which is utilized for patient-specific drug therapy and is exemplified by metabolism impairment due to liver or kidney disease, the organs which eliminate drugs from the body. In patient's with advanced age, or with reduced liver or kidney function, many drugs are metabolized by the body at a reduced rate. Accordingly, with impaired kidney or liver function, or extremes of age, drug doses need to be frequently reduced in order to avoid over-dosing. Dosage adjustments, necessary if the drug is to be metabolized by either organ, is determined according to well-defined tables which correlate the dose adjustment against common indices of degree of liver or kidney impairment.

In particular, U.S. Pat. No. 5,833,599, entitled "Providing Patient-Specific Drug Information" is directed to this most simplistic form of drug administration decision support, namely the ability to calculate drug dosage adjustments when elimination or metabolism of a drug is decreased specifically due to liver or kidney dysfunction. This particular reference describes a system which determines a modified dosage and/or alternative therapy on the basis of certain patient-provided information, including the patient's age, kidney function and liver function.

In addition to being relatively simplistic and directed to specific dysfunctions (i.e., liver or kidney impairment) there are a number of possible adverse interactions involving drugs which do not relate to specific metabolism dysfunctions or relate to metabolism impairment of which kidney disease, liver disease, or advanced age, are only a minute subset. For example, certain drugs need dose adjustment when other drugs are concurrently taken, when patients are smokers, when certain laboratory test abnormalities are noted. In addition, some drugs can be dangerous during pregnancy or breastfeeding (conditions and not diseases or dysfunction), while quite safe otherwise. Also, certain drugs can be dangerous in the context of disease which is completely unrelated to the metabolism of that drug. For example, patients with marked thrombocytopenia (a decreased number of platelets, which are responsible for the clotting of blood) should never receive the blood thinner medication called Coumarin, as the resulting combination can cause spontaneous bleeding into the brain, often resulting in stroke. In this particular scenario, the clinical condition of thrombocytopenia is completely unrelated to the metabolism of Coumarin by the liver, kidney, or age-related factors.

It should be understood that prior art-type drug-drug and drug-metabolic interaction tables and/or electronic systems which embody them, are very limited in nature, and incomplete in terms of considering all clinically important patient dimensions simultaneously. For example, if a person possesses the gene BRCA1 in his/her DNA, or is a heavy smoker, dosage adjustments (or abandonment of drug therapy all together) may be warranted for particular drug therapy regimens. In no system existing today can all of the relevant clinical dimensions impinging on a drug therapy regimen be accommodated simultaneously. To do so requires a unified data model of the patient in which all possible states of each particular dimension are defined symbolically and numerically (mathematically) ordered. A unified patient data model would then allow for machine-based symbolic reasoning and automatic calculation of the most appropriate choices for drug therapy, including necessary dosage adjustments for each chosen drug. The decision on which drug to use in the first place, for example, is often based on a drug's efficacy in a specific situation, that is defined by subsets of all possible dimensions. For example, use of aspirin for stroke prevention in a patient with low blood platelet count is dramatically different from a person who has a normal platelet count. Finally, such a system must consider certain economic factors, such as whether or not the medication chosen is covered by a patient's health insurance provider (referred to as the approved drug formulary).

DESCRIPTION OF THE DRAWINGS

These and other features, aspects and advantages of the present invention will be more fully understood when considered in connection with the following specification, appended claims and accompanying drawings wherein:

FIG. 4 is a simplified graphical representation of a Medications and Allergies dimension, indicating their role in symbolic reasoning and including a severity qualification according to the invention;

FIG. 5 is a simplified graphical representation of a Review of Symptoms dimension and its role in symbolic reasoning;

FIG. 6 is a simplified graphical representation of Vital Signs, Physical Examination and Diagnostic Test dimensions and their role in symbolic reasoning in accordance with the invention; and FIG. 7 is a simplified graphical representation of a proposed medication list for a proposed drug therapy characterized in terms of an efficacy score, a contraindication score, an economic score and appropriate dosing.

DETAILED DESCRIPTION OF THE INVENTION

Figure 1:
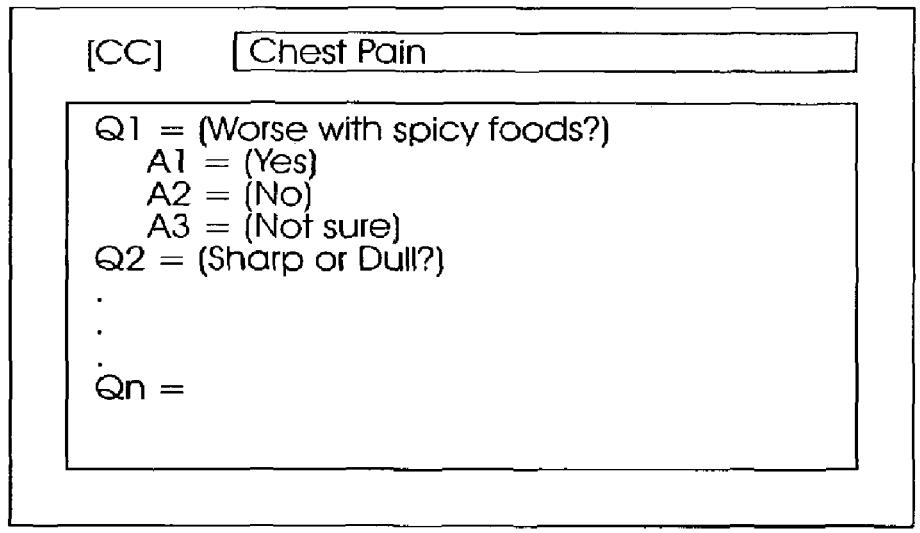
FIG. 1 is a simplified graphical representation of a History of Present Illness (HPI) dimension and associated qualification strings useful in developing a diagnosis in accordance with the present invention.

The present invention relates to a system and methodology by which patient-specific, clinically-optimized drug therapy regimen may be determined using a computer by taking all of the clinical dimensions relating to that patient into account when developing a drug therapy regimen. Clinical dimensions are defined by vectorized indices and therapy is optimized by performing simultaneous symbolic reasoning across all clinical dimension vectors. In terms of a clinical reality, a physician evaluates a finite, well-defined set of input variables, the arguments of which are determined during a patient interview and history analysis, in order to inform the system with regard to that particular patient. In accordance with the present invention, these input variables are associated to the clinical dimensions which optimize a particular drug or medical therapy regimen in accordance with "rules" developed from a universal body of medical knowledge. Necessarily, the clinical dimension vectors are interrelated, with one or more dimension having a particular, characterized effect on one or more of the other dimensions, according to an invoked "rule". Each dimension necessarily has a corresponding set of rules by which they are interrelated to the other dimensions.

For example, a co-existing disease, like a heart murmur, can preclude the use of a given drug (e.g., an allergy medicine) entirely due to a life-threatening drug-disease interaction. Similarly, a genetic condition, such as the presence of the BRCA1 gene in one's DNA, may preclude the use of estrogen for hormone replacement. Additionally, a low serum sodium condition can make some medications dangerous; certain dosages of certain drugs may need to be adjusted in smokers, even if they do not have any diseases caused by smoking. Without a unified data model which also uses symbolic representations of knowledge, as described herein, all important inter-relationships cannot be simultaneously considered.

Summarized, there are several specific clinical dimensions which are often used simultaneously by physicians in order to determine a drug or medical therapy regimen. Each of these clinical dimensions dramatically influences a physician's decision on which medications are to be considered when treating a patient, what dosages should be employed and what, if any contraindications are suggested by any combination of clinical dimensions existing for a particular patient.

In the context of the invention, there are twelve specific input clinical dimensions which are simultaneously analyzed in accordance with symbolic reasoning in order to optimize a drug therapy regimen. The twelve dimensions (which might also be considered as input variables) are exemplified by the following: Chief Complaint (CC), History of Present Illness (HPI), Past Medical History (PMEDHX), Past Surgical History (PSURGHX), Family History (FAMHX), Social History (SOCHX), Medications (MEDS), Allergies (ALLER), Review of Symptoms (ROS), Vital Signs (VS), Physical Exam (PE), and Diagnostic Tests (LAB). Each of these dimensions is understood by all clinicians in a heuristic fashion, and the abbreviations used above are those generally accepted by medical practitioners. However, the present invention rigorously uses each dimension in the context of machine symbolic reasoning, as described below.

Each of these clinical dimensions are related to a universal body of medical knowledge, termed herein the "Rule Book of Medicine" in a manner described further below. This "Rule Book", for purposes of the present invention, is finite, and does not necessarily comprise to the totality of medical knowledge, but rather the standard of medical care as defined by regulatory agencies including the Food and Drug Administration (FDA), the Center for Drug Evaluation and Research (CDER), the National Institutes of Health (NIH), and the US Preventative Task Force (USPTF). It may also be selectively enhanced by including rules published by each of the major medical speciality societies regarding what they deem to represent the standard of care for various clinical circumstances. It should be noted that once the above twelve dimensions are rigorously defined according to symbolic representation as described in the present invention, that essentially all medical rules can be converted into a symbolic representation which thereby enables machine reasoning.

Examples of such rules (and the dimension they point to) include the following statements:

Avoid Drug X in patients with chest pain (MEDS→CC);
Avoid Drug X in patients with strong family history of breast cancer (MEDS→FAMHX);
Reduce the dosage of Drug X in patients who are smokers (MEDS→SOCHX);
The dose of Drug X in children is 25 mg per kilogram of weight (MEDS→VS);
Avoid Drug X in patients who are pregnant (MEDS→PMEDHX);
Avoid Drug X in patients with penicillin allergy (MEDS→ALLER);
Reduce the dosage of Drug X by 25% if the patient is positive for the genetic marker HLAB27 (MEDS→LAB);
Use Drug X with caution in patients with edema (MEDS→PE);
Avoid Drug X in patients also taking Drug Y (MEDS→MEDS);
Discontinue Drug X in patients with recent weight loss (MEDS→ROS);
Administer HIB vaccine in a child over the age of 2 (MEDS→VS); and
Check all patients white blood count every month if taking Clozaril (LAB→MEDS).

It should be noted that each statement represents a simple rule between two dimensions, but that more complex rules can be constructed using the same framework and use of Boolean logic which can be represented as symbolic machine language to enable reasoning to occur.

The input clinical dimensions have been chosen as representing particular categories of medical knowledge that a physician might (or more properly, should) consult (either alone or in combination) when making a medically relevant decision.

The Chief Complaint (CC) dimension corresponds generally to a subjective symptom reported by a patient or physical finding made by a physician. Examples of Chief Complaint dimensions might include chest pain, nausea, tinnitus (ringing in the ears), rash, lightheadedness, syncope (fainting), or the like. Subjective symptoms or physical findings are preferably classified in accordance with a robust medical language like SnoMed™ (generally recognized as among the most robust databases; compiled by the American College of Pathologists). Ontogeny becomes important since subjective symptoms can often be represented in vague terminology (e.g., foot swelling) which might have multiple etiologies or subsets. It is important to recognize that many subjective symptoms or physical findings will cross-reference to the most widely used classification of disease, known as the ICD9 (International Classification of Disease, Ninth Edition). However, the ICD9 is a macro-list of broad clinical terms used primarily for insurance billing purposes, and is physiologically incomplete from the perspective of medical decision support. Even if ICD9 were complete from a scientific perspective, ICD9 and SnoMed are merely a catalog of terms, and not a decision support/inferencing system. As will be developed further below, the contents of ICD9 and/or SnoMed contribute to what is termed the "Rule Book of Medicine" in that they contain a list of terms which physicians recognize as identifying various medications, diseases, conditions, and the like, as well as certain synonyms for those terms and various categories of medications, diseases, conditions, etc. into which various other terms may be classified.

Regardless of the classification system used, the classification terms are developed, from the classification source (e.g., SnoMed™) in combination with input received from the generalized community of users (e.g., other practitioners), and maintained in a database. Database items are relationally structured and are available to the system user by associative extraction techniques, well understood by those having skill in the art of database construction. Thus, a CC of "chest pain" can be extracted by merely indicating "c", or "ch" with a keypad, stylus or the like, with the system presenting the practitioner with an alphabetical list of choices. The practitioner makes a selection from the list and enters the selection as the Chief Complaint (CC) associated to that particular patient.

Clinically, it is important that a physician not overlook the various possibilities that obtain for each symptom. Even though a subjective symptom might imply a relatively benign condition, certain possibilities associated with subjective symptoms might be serious. For example, in a patient with chest pain, a physician must not exclude the possibility of undiscovered severe heart disease. A physician might overlook a spicy meal eaten the day before, but must not overlook a heart attack in progress.

The Chief Complaint (CC) dimension is particularly important for the development of a list of diagnostic possibilities (also known as a differential diagnosis and termed DDx herein) that should be considered for each of the subjective symptoms or physical findings. Generating a differential diagnosis, in the context of the invention, precludes the physician from overlooking an important diagnosis and, more particularly, from overlooking a particular potential disease with which a particular drug treatment regimen may interact. For example, a hypothetical Drug X may be contraindicated in patients with angina (chest pain), a CC dimension.

The History of Present Illness (HPI) dimension relates to particular questions asked to the patient specific to the Chief Complaint discussed above, and related to it. Each particular string of questions has a unique symbolic representation and a well-defined set of possible values. Since there is no currently existing data base which provides a standard, uniform string of questions (e.g., worse with spicy foods?), a unique data base is provided, in the context of the invention, in which each string of questions has a unique representation and a set of possible result values for each Chief Complaint. For example, and in accordance with the embodiment depicted in FIG. 1, in connection with a CC of chest pain, the HPI dimension are represented by a string of questions Q1, Q2, ... Qn, each having a well-defined set of possible result answers. Q1 might equal the string "worse with spicy foods" to which the possible answers (A1, A2, A3) might be yes, no, and not sure, respectively. Q2 might equal the string "history of trauma to the chest" with result values (A 1, A2 and A3) being serious, minor or no, respectively. The query response canto continues until the final question Qn is cleared with a noted response.

The use of a particularized data base of HPI for specific Chief Complaints, allows for a nurse or medical assistant to offload the physician's time, by making routine inquiries of the patient. Specifically, one does not need to be an M.D. in order to ask questions like "is the chest pain worsened by spicy foods." In addition, without recourse to the present invention, a physician might frequently forget to ask key questions about the Chief Complaint until the patient has already left the office and further fail to do so at a later time. Answers to particular questions relating to the Chief Complaint are a particularly key to making an accurate diagnosis and are particularly useful when the HPI are used in combination with the CC to narrow generation of a differential diagnosis (DDx) for a particular patient.

In this regard, the various questions comprising the CC qualifiers (HPI) are again maintained in a database, with each question set associated to a particular CC or a set of CCs. The question sets themselves include clinically relevant questions that are well known to physicians. The sets are developed by aggregating input from the general user community and expanded as needed through a centralized upload/download facility, thereby making the latest question sets available to all users on an immediate basis.

The Past Medical History (PMEDHX) dimension is a list of co-existing, known diseases associated with a particular patient. In an ideal situation, a physician is able to determine each disease in a rigorous fashion (in accordance with a SnoMed classification, for example) but in most practical scenarios, co-existing diseases will likely be numerically encoded in accordance with ICD9 definitions, since these are insurance industry standard codings which a physician has likely used for billing purposes. Additionally, there will be patients for whom no rigorous medical history has been developed, but the patient believes they know what he/she has.

In accordance with the invention, there might be two categories of responses to a PMEDHX dimension, a limited utility response, such as "heart problem" and a non-ideal, but high utility response, such as "high blood pressure." Ontogeny can be particularly useful in this particular context, since PMEDHX is, along with Medications (MEDS), one of the more crucial patient dimensions in terms of prevention of catastrophic medical errors. Co-existing disease has a particular clinical implication when it is understood that a co-existing disease, combined with a medication, can be lethal or cause serious or irreversible harm.

Co-pending patent application entitled Computerized System and Method for Rapid Data Entry of Past Medical Diagnoses describes a system and methodology by which data fields relating to a particular patient's current medications and/or allergies allow their past medical diagnoses to be rapidly entered into an electronic database with minimal cost and minimal time commitment on the part of the physician. Data entry is performed in accordance with a computerized reverse-indexing system that utilizes an intermediate, medication indications database, combined with concept-matched specific diagnoses extracted from a conceptual database, where the specific diagnoses are identified in accordance with detailed medical terminology such as might be expressed in the ICD9 or some other medically robust catalog of medical disease classifications. In addition to providing enhanced efficiency, the accuracy and rigor of standard medical terminology, particularly with regard to a patient's past medical diagnoses, is preserved.

The methodology, in accordance with the invention, utilizes an initial data entry of current medications and known allergic responses, ideally made either by the patient themselves providing the information, or by a medical assistant (to expedite clinical workflow) in consultation with the patient. However, a physician is necessarily also enabled to do so. This initial data set of medications and/or known allergic responses, is then electronically processed by a computer, or other purpose-built processing engine, and the list of medications and/or known allergic reactions, is reverse-indexed using a concept-matching intermediate database, to a set of macro diagnoses. In the context of the invention, a macro diagnosis represents one of a multiplicity of broad conceptual reasons why the medication might have been prescribed. A conceptual macro diagnosis is selected from the presentation, and once selected, a specific set of discrete diagnoses is then presented, each associated to the selected conceptual macro diagnosis, with sufficient rigor of terminology, such as might be found in the ICD9 database.

Thus, significant portions of PMEDHX can be easily and quickly established by a practitioner, particularly those portions that have some present representation and for which a patient is currently taking a known medication. A robust definition of PMEDHX is especially important since a well defined PMEDHX allows satisfaction of certain clinical implications as depicted in the exemplary embodiment of FIG. 2. Exacerbation of an existing disease may be the cause of the Chief Complaint (CC), thereby allowing a direct correlation between CC and the most relevant differential diagnosis (DDx). Also, co-existing disease may have implications for certain proposed medications relating to the CC; certain medications can be lethal when combined with co-existing diseases. The same is true for medical conditions; co-existing disease combined with low serum sodium can be quite harmful and even fatal.

Accordingly, PMEDHX necessitates certain procedures. PMEDHX implies condition interaction screening to insure that medical conditions that would exacerbate a co-existing disease are discovered and adequately treated. PMEDHX also implies drug/condition interaction checking to insure that prescribed medications are compatible with a co-existing condition. Certain co-existing diseases also imply a screening regime; annual screening to prevent blindness in diabetics, for example. Thus, the PMEDHX dimension represents a powerful tool for not only DDx development, but also for general health maintenance. Necessarily, PMEDHX dimensions are represented as individual items in a database, with each database item identified as a disease code (whether ICD9 code or some other recognized disease classification system). Further, and as will be described below, the necessitated procedures are informed by a set of "rules" that are defined in and constructed from that universal body of medical knowledge termed the "Rule Book of Medicine". These "rules" are the summation of procedures, suggestions, recommendations, indications and contraindications, that have been developed by the medical community over time, and represent the standard of care with respect to medical decision making.

The Past Surgical History (PSURGHX) dimension relates to surgical operations performed on the patient. All surgical operations are clinical procedures which are classified by various standard catalogs, such as the American Medical Association's Current Procedural Terminology (CPT™) coding system. Each possible surgical procedure has numerical ID associated with it and most will have been coded as CPT definitions, since these are the ones a physician has likely used for billing purposes. In a manner similar to Past Medical History, above, there will be a certain number of patients for whom no rigorous surgical history has been developed, but the patient believes they know what he/she has had performed. Unlike the Past Medical History context, patients generally have a very accurate idea of what they have had done surgically.

Figure 2:
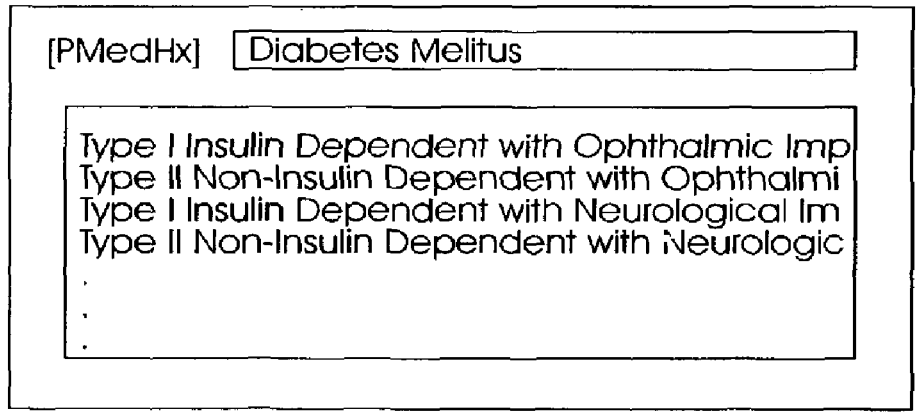
FIG. 2 is a simplified graphical representation of Prior Medical History and Prior Surgical History dimensions indicating their role in symbolic reasoning according to the invention.

The clinical implications of the Past Surgical History dimension have a limited utility outside a diagnostic artificial intelligence application, but are particularly useful, in the context of the invention, in further narrowing a differential diagnosis (which can determine initial empiric drug therapy) and/or developing a condition interaction or further refining a drug-disease interaction as depicted in FIG. 2. In particular, associated complications might be determined as the cause of the Chief Complaint (e.g., maldigestion due to removal of stomach). Associated conditions could be caused by a surgical procedure (e.g., anemia following stomach surgery) and differential diagnoses and associated probabilities can be included or excluded based on a past surgical history. For example, stomach pain cannot be due to an infected gallbladder if it has already been removed surgically. Hence a medication such as ursodiol, commonly used to treat gallstones and their symptoms, is not an applicable therapeutic option.

Figure 3:
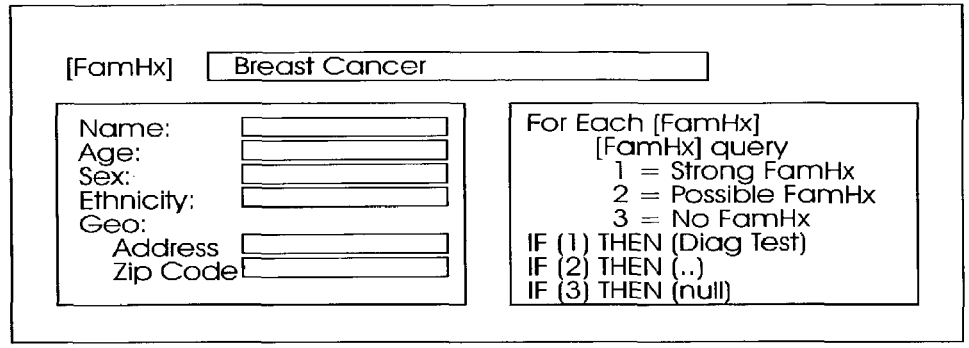
FIG. 3 is a simplified graphical representation of Demographic/Family History and Social History dimensions indicating their role in symbolic reasoning and including a severity qualification according to the invention.
Figure 3:
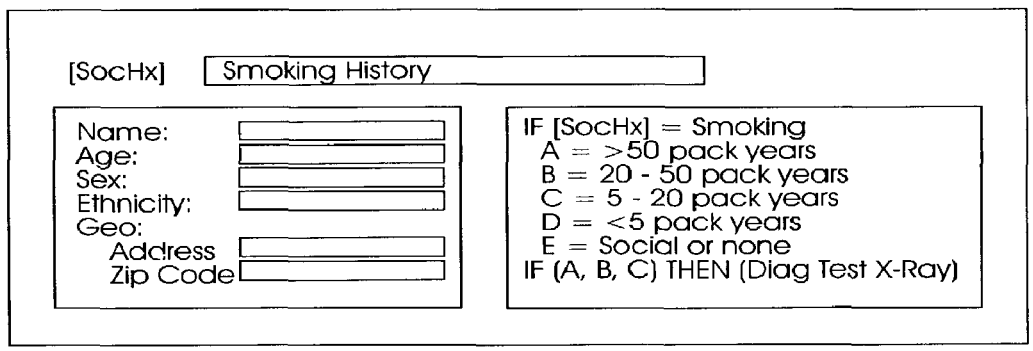

The Family History (FAMHX) dimension is a data set of known genetically-based health abnormalities which can be represented symbolically along with a strength of association as a weighting option (all close relatives versus rare, distant relatives), as indicated in the embodiment of FIG. 3. Presently, there is no conventional data base of FAMHX terms. Such a data base is created and mapped to Snomed terms at the highest level of ontological classification (e.g., family history of heart attacks). Strength of association is carried as a weighting factor. For example, a family history of breast cancer might be identified as the set header "breast cancer," with weighting factors A, B, . . . X, Y, referring to association strings such as "A=strong family history in near relatives, B=strong family history in distant relatives, . . . X=possible family history, and Y=no history," or the like.

Clinically, positive family history has certain implications for patient treatment in general and optimization of a drug therapy regimen in particular. Positive family history can be correlated to an increased likelihood of the disease being present which narrows the differential diagnosis or increases the probability of a specific diagnosis within the DDx. Further, a positive family history for specific diseases necessitates appropriate medical management, e.g., if the argument to FAMHX equals breast cancer is A=strong family history in near relatives, and the patient is female, a mammogram is indicated every six months. This is a particular example of a "rule" found in the "Rule Book of Medicine". Simply stated, the "rule" is that females with a family history of breast cancer should have a mammogram every six months. In the context of the invention, this "rule" is expressed in symbolic logic, with certain of the input clinical dimensions being "arguments" for "rule" variables.

The Social History (SOCHX) dimension is substantially similar to the FAMHX dimension described above, but rather corresponds to certain social factors such as use of tobacco, drugs, alcohol, occupational exposures to asbestos, coal dust, and the like. It is contemplated that there are approximately 200 SOCHX data elements which will comprise the top level elements of an SOCHX data base, with elements collected and aggregated from collective inputs of the general community of users. Each of the data elements can be symbolically represented into distinct categories. For example, if the data element represents smoking history, it can be further categorized in accordance with a severity metric which might range from A=>50 pack years to E=rare or social use only, as indicated in the example of FIG. 3.

Clinically, the presence of a severity metric related to a Social History data element tends to increase the likelihood of a disease, associated with that data element, being present. Effectively, an appropriate Social History metric narrows the differential diagnosis or increases the probability of a specific diagnosis within the differential diagnosis (DDx) and determine initial empiric therapy. Further, a positive SOCHX for specific diseases necessitates appropriate medical management in a manner similar to FAMHX, described above. Particularly, if the data element "smoking history" has a severity metric of A=>50 pack years, B=20-50 pack years, or C=5-20 pack years, a chest x-ray every 18 months is indicated; another example of a "rule".

Turning now to the example of FIG. 4, the Medications (MEDS) dimension is one of the most critical dimensions that a physician needs to consider in the course of developing a drug therapy regimen for a particular patient. The importance of this dimension in a clinical setting will be particularly understood when it is considered that side effects of medications can often be the cause of the Chief Complaint. Further, medications combined with other medications (drug-drug interactions) can be lethal or cause serious or irreparable harm in certain cases. Similarly, medication combined with a medical condition (such as low serum sodium) or with a medical disease (heart murmur) can be lethal or cause serious or irreparable harm. In a statistically significant portion of the patient population, certain medications require screening for serious side effects which, if not performed, can have lethal or serious and irreparable consequences. Each of these interactions can be found within the "Rule Book of Medicine", and are generally well understood by those having skill in the medical arts.

All FDA approved medications, for use in America, are classified according to the National Drug Code (NDC) catalog and each are assigned a unique numerical ID. Further classification of each medication is based on regimen (frequency and dose) which have implications for recommendation of other therapies due to possible interactions. It should also be understood that the "effective" dose of a medication is also a function of the route by which it is introduced. In terms of the "Rule Book", this information may be developed from, for example, drug labeling instructions available from the FDA as well as Class 1-2 guidelines developed by the U.S. Preventative Task Force. These are considered official recommendations due to strong (stastistically-signficant) evidence in controlled studies. Other sources of interaction information will suggest themselves to those familiar with the field.

Medication entry into the system of the invention includes all of the above-noted classification options. For example, a particular medication entry might be Penicillin Potassium (ID=2492311), 500 mg., 4 times per day, orally. Thus, MEDS are evaluated in accordance with their identifier, dose, frequency, and introduction route.

With further reference to FIG. 4, the Allergies (ALLER) dimension is also of particular importance in the context of the present invention. It is well known that allergic reactions often have fatal consequences. Additionally, there are approximately 300 broad classifications of ALLER data elements of which patients will likely be aware. These include reactions to dust mites, food substances, copper, pollen, or bee stings. In addition, there are known specific allergic reactions to medications, most of which are contained in the National Drug Code (NDC) catalog. Some additional complexity is introduced because if a patient states an allergy to Morphine, for example, there might be over twenty specific medications that contain Morphine or have a cross-allergy indication (a beta-lactam cephalosporin with Penicillin, for example).

A unique symbolic element is created for each type of allergy, whether food, drugs, a drug class or environmental factor. The impact of that allergy element on a particular patient is scored according to the severity of that patient's reaction. For example, a particular patient might have an allergic reaction to Penicillin with a severity of 2, but an allergic reaction to copper with a severity of 9. Another patient may have an allergic reaction to copper of 1, but an allergic reaction to the sulfa drug class of 7. Thus, the ALLER dimension is particularly important in narrowing or strengthening a differential diagnosis, but even more particularly important in developing and/or defining an allergy-drug interaction metric.

The Review of Symptoms (ROS) dimension relates to a list of broad questions that are generally related to CC, but are more conceptual in nature. A well-performed ROS is able to uncover additional medical problems which the patient may have apart from the one he/she is visiting the physician for. An ROS is exemplified by the screening questionnaire a patient often completes when visiting a physician's office for the first time. Exemplary such questions include "do you have any unintentional weight loss?, fever?, etc." The data base elements relating to ROS are generally short and comprise approximately 2,000 data elements which are generally well known to those having skill in the art. Comprehensive summaries of ROS elements can be found in many standard medical textbooks and need not be further described herein.

A positive ROS is also able to generate a second differential diagnosis, independent of the CC, which should demand a physician's attention. Quite commonly, a patient may consult a physician for a CC for a relatively minor complaint, a cut finger for example, and an ROS discovers another serious illness (a heart problem exposed by chest pain) unrelated to the Chief Complaint. Practically, because ROS are questions, most can be asked by a nurse or medical assistant in layman's terms, thus removing some of the work load from the physician. Again, it should be noted that initial drug regimens are often empiric and based on symptomatology suggesting a most probable diagnoses, even when an exact diagnosis is not known. Hence it is important to be able to include subjective, physical exam, family, and social history dimensions into a computerized system when determining initial treatment regimens that are patient specific and also optimized based upon context.

In the case of pharmacotherapy, the ROS dimension plays an important role as frequently one drug is commonly used to prevent the side effects of a co-administered drug. For example, persons taking high dose steroids for immune deficiency disease will often need anti-acid therapy (and often quite aggressively) to prevent stomach ulceration. If these persons describe having abdominal pain or have iron-deficiency anemia present (signs of a bleeding ulcer), the co-administered anti-acid regime may well require re-evaluation.

The Vital Signs (VS) dimension includes objective, numerical demographic parameters such as a patient's age, sex, weight, blood pressure, heart rate, respiratory rate and height. Since these parameters are all objective numerical values, no data base is necessary and they may be entered directly into the system.

Important medical criteria for screening for important diseases are often associated with the age metric. Even in the absence of disease, age is associated with important changes in the effectiveness and dosing of various drugs. Similarly, weight, blood pressure and heart rate will often inform a drug therapy regimen, particularly if the drug is devised as affecting one of these metrics. High blood pressure and heart rate, for example, will often preclude use of certain weight reduction drugs. In pediatrics, weight is typically the most crucial dimension in terms of drug dosing.

The Physical Exam (PE) dimension relates to the presence or absence of physical exam findings which, in turn, are able to increase or decrease the probability of a particular disease being present. This, in turn, can affect the choice of medications to be employed in any particular drug therapy regimen. For example, a critically ill patient with a systemic petechiae (bruising) is likely to have a blood coagulation disorder and hence should not be administered medications which may cause further thinning of the blood. The presence of certain physical exam findings may have implications for appropriate diagnostic evaluation (particularly in the context of a differential diagnosis). A narrowly defined differential diagnosis has further implications on a drug therapy regimen, as will be described in greater detail below.

Lastly, the Diagnostic Tests (LAB) dimension is directed to results of diagnostic tests such as serum chemistry, blood count, and x-rays. There are currently about 10,000 diagnostic tests available to the contemporary physician, of which approximately 500 are commonly performed.

The results of diagnostic tests can dramatically affect a particular drug or medical therapy regimen. For example, a patient with a very low serum sodium should not receive a mediation which has a side effect of lowering sodium even further. This is potentially lethal. Alternatively, if the patient is positive for possession of the BRCA1 gene, it may alter the specific components of chemotherapy desired for breast cancer treatment. Indeed, it is likely that the future of medical therapy for cancer will depend upon the genetic makeup of the particular individual.

In a manner similar to the definition of the input variables (clinical dimensions), there are a finite well-defined set of output variables, that determine what a physician might do with respect to a particular patient's treatment. These output variables can be categorized as one of five well-understood possible interventions and may be further granularized in terms of a preferred order of choice. The output variables (dimensions) are (1) a counseling dimension, (2) a pharmacotherapy dimension, (3) a procedural therapy dimension (which includes surgeries), (4) diagnostic testing recommendations and (5) specialist referral.

All of the output dimensions are inter-related in a well understood fashion. For example, a medication that a patient is currently taking can require that diagnostic tests be performed at regular intervals to minimize the possibility of medication-induced organ system damage; an example of the relationship between medications and diagnostic testing. A further example involves drug/disease interaction, in which a class of drugs known as beta blockers is commonly prescribed to treat high blood pressure. However, beta blockers also precipitate asthmatic attacks and therefore should never be prescribed to severe asthmatics.

In operation, the system, according to the invention, operates upon the various clinical dimensions (input variables) described above, in order to make determinations as to any possible drug-drug, drug-disease, drug-allergy, drug-condition, and drug-diagnostic test interactions that apply and further to make recommendations as to a set of particularly effective and safe drugs in any given case, and the appropriate dose. These operations are performed in accordance with a table or database element set of inter-dimensional relationships (rules) that define known and characterized drug-drug, drug-disease, drug-condition, drug-allergy, or drug-diagnostic test interactions, for example.

The various rules which govern the methodology of the present invention are derived from the "Rule Book of Medicine" which contains a compilation of recognized medical therapies, including medication therapies, as well as an indication of absolute and relative contraindications for the various therapies and medications. The "Rule Book of Medicine" is generalized term which subsumes all of the information contained within the various references described above, the Physician's Desk Reference, for example, as well as the various drug labeling instructions, approved and disseminated by the USFDA, including absolute and relative contraindications as defined (approved) by the FDA. Additionally, the "Rule Book of Medicine" includes Class 1 and Class 2 guidelines as defined by the US Preventative Task Force. As will be understood by those having skill in the art, additional sources of therapeutic references may also be added to the "Rule Book of Medicine" in order that the rule book be as complete as possible with respect to the universe of medical therapeutic knowledge.

Initially, the methodology of the invention defines the medical "rules" as found in the rule book in terms of symbolic logic and also with respect to the actual language found in the rule itself. This last is necessary because there is presently no consistency of terminology from rule-to-rule. Because of this inconsistency, it is desirable to have every rule term listed in the rule database, for example, with pointers linking thesaurus equivalents to one another and also grouping various equivalent terms into classes or categories, for which any given term might be a subset. As will be described in greater detail below, concept normalization of inconsistent medical terminology is an important feature of the methodology of the invention and supports a particularly efficient form of decision support.

In context of the invention, all of the medical terms which are found in the "Rule Book of Medicine" are listed in a relational database. As a term is listed, it is initially determined whether that term is a categorical term or an "irreducible medical term". For purposes of this specification, a categorical term is defined as one which includes a plurality of irreducible medical terms, many of which may be different, and many of which may be synonymous with one another. An irreducible medical term is defined as one which may have a synonym or synonyms, but which nevertheless completely identifies a particular relevant medical item such as a specific drug, a surgical procedure, a particular disease, condition, and the like.

For example, bacterial meningitis is a well recognized term for a particular disease. Accordingly, bacterial meningitis might be viewed as an irreducible medical term since it identifies a particular disease (bacterial meningitis) and no other. Meningitis has a number of synonyms which might be found in various rule book terminology; examples of such synonyms are infectious meningismus and I.M. Accordingly, when the terms I.M., infectious meningismus and/or bacterial meningitis are found in various rules, pointers link these terms together as synonyms and also identify the term bacterial meningitis for example, as the irreducible medical term to which these synonyms relate.

It is also well understood that the disease meningitis is one of a number of central nervous system diseases (alternatively central nervous system disorders) allowing bacterial meningitis to be classified within a class or category of central nervous system diseases. Thus, it should be understood that the class of central nervous system diseases would include the irreducible medical term meningitis, as well as other irreducible medical terms relating to various other specific diseases subsumed within the classification or category of "central nervous system disorders". It is also axiomatic that these other irreducible medical terms will also necessarily have various synonyms, as will the classification "central nervous system diseases" itself. Thus, the database will be understood to define many-to-many relationships between and among its content items.

Taking the classification system to yet an additional conceptual step, it will be realized that meningitis is also subsumed within the classification of "spinal cord and brain diseases", as well as the classification of "severe infections". Additionally, meningitis may be categorized as an "inflammation of the meninges". Indeed, meningitis might be categorized as belonging to any one of a number of different general classifications, depending solely on whether that classification term appeared in any of the rules developed from the universal "Rule Book of Medicine". Specifically, if the term "inflammation of the meninges" was found anywhere in the "rule book", that term would be included as a classification in the database of the present invention. Thus, category or classification definition is driven by the contents of the rule book and not by an arbitrary structural definition. Likewise, synonyms to an irreducible medical term are also driven by the contents of the rule book. As any term is developed from the rule book, it is entered into the database and a determination is made whether it is a synonym to an irreducible medical term, itself an irreducible medical term, or a categorical term within which irreducible medical terms, or even other categories, are collected.

Thus, for all terms entered, concept normalization involves definition of all equivalent terms for the entered term as well as definition of all classes or categories for which the term is a subset. As an additional example, the term hypokalemia is equivalent to "low serum potassium" which is, in turn, a subset of the category of "electrolyte disorders". Electrolyte disorders represent a class or category of disorders of which low serum potassium and/or hypokalemia are subsets. In this particular case hypokalemia might be identified as the irreducible medical term for which low serum potassium is a thesaurus equivalent.

Medical term entry is further performed as part of a medical rules definition process, in which each of the medical rules found within the "Rule Book of Medicine" are defined in terms of symbolic logic. For example, one of the rules that might be found in the universal body of medical knowledge, is that the use of Demerol™ in a patient taking phenelzine can cause life threatening seizures and these two medications should never be administered together. In terms of symbolic logic, this particular rule might be written as:

IF (drug)=[Demerol] AND (drug)=[Phenelzine] THEN [Flag]

In this particular case, [flag] might represent a pointer to an absolute contraindication, a relative contraindication, or might indicate that the combination of the two drugs are okay (i.e., a [NULL FLAG]). It is also informative to recognize that the argument of the IF and AND expressions is characterized in symbolic terms as an undifferentiated drug. In terms of the invention, the input clinical dimension (MED) will be understood to substitute for the argument (drug). Thus, the "rule" is made relevant to any medications taken by a particular patient. All that is required to invoke the rule is that a patient have an input dimension that corresponds to the argument (drug). If the (MED) dimension includes an entry, but not for either Demerol or Phenelzine, the results for the IF and AND expressions are [NULL]; thereby giving a [NULL FLAG]. In other words, the rule is not invoked. It should be emphasized that in the present invention (by its very construction), all rules can be converted to reasoning-enabled symbolic logic as all possible dimensions have been defined and symbolic terms assigned to each possible variable, and a meta-thesaurus of synonyms and ontogeny are included to avoid ambiguity.

Each of the rules found in the "Rule Book of Medicine" are expressed in this form and all of the terms found within the rule are added to the terminology database. Equivalents are set for categories and irreducible medical terms; categories are assigned to categories; irreducible medical terms are assigned to categories; and irreducible medical terms are also assigned to irreducible medical term equivalents (synonyms), if appropriate, in accordance with each rule. Necessarily, the number of equivalent terms, as well as the number of categories are defined by the rules themselves.

In order to simplify the process, each of the terms contained within the terminology database are assigned a unique set of symbols. The symbols might be numeric or alphanumeric, or any other unique symbology set, so long as each term is converted into a unique symbol, including all medical terms and all medications. By way of example, the term "penicillin" might be assigned the symbol "126473" while its equivalent forms "trade names, salts, and the like" would each be assigned a different symbolic representation, as would the class of Beta Lactam drugs of which it is a subset. In this regard, use may be made of identification codes found within ICD9, or other suitable classification source, but only if they result in every term having a unique symbolic value.

It should now be realized that the various clinical dimensions discussed above have a direct relationship to the terms and terminology used in connection with rules defined in the "Rule Book of Medicine". For example, the MED dimension relates to medications and or drugs, and an initial data entry associated to the MED dimension will necessarily invoke one of either the irreducible medical terms or equivalent terms associated to the particular drug or medication entered. Likewise, the PMEDHX dimension relates to terminology found within the rules that corresponds to aspects of a past or present medical history, for example, pregnancy. Similarly, terms associated with allergies (the ALLER dimension) and a surgical history (the PSURGHX dimension) are all assigned a corresponding database entry and unique symbol representation, such that any "rule" (by definition) expressed in language form can also be expressed in terms of logical symbology which can be implemented using a computer.

It should therefor be understood that input dimensions contain terms or terminology that invoke one or more rules that are identified by a commonality of variables. For example, if the MED dimension contains the variable Accutane, the unique symbol associated to Accutane is extracted, matched with all of the unique symbols associated to either its equivalents and/or categories, and those unique symbols used to extract all rules associated to those symbols. In this particular case, all rules having an expression IF (MED)= [11122233], (where 11122233 is the symbol for Accutane) will be identified and invoked for further analysis. It should also be understood that additional rules, written in terms of Accutane equivalents and/or (MED) categories which contain Accutane, will also be identified and invoked for further analysis. In many cases, the combinatorial logic of the rules will allow many if not most of the additional rule sets to be subsequently "nulled", by analysis of additional AND, OR, AND NOT, logical expressions. As will be described in greater detail below, the "IF" "THEN" symbology allows for multiple combinations of input dimensions to be concatenated in order to arrive at an output result. In accordance with the present invention, if any rule is invoked by an input dimension, that rule will be reasoned.

In the present invention, important inter-relationships between the clinical dimensions are mapped topologically in accordance with developed rules, and might further be encoded with a severity score which signifies the strength of the link. For example, the presence of the drug Clozaril™ (MED dimension) is linked to the LAB dimension for the diagnostic test known as the complete blood count (CBC) which is used to test for the drug's serious side effect. The strength of the association is stratified according to severity score, in which the relationship might be characterized as (1) weak, (2) strong, or (3) mandatory. A multitude of severity scores can be used with differing weights based upon clinical utility, FDA recommendations and well understood guidelines such as those developed by the U.S. Preventative Task Force.

The strength of an association (severity) can be either subjective or objective, based upon the body of knowledge which supports the recommendation. For example, the FDA may state that all patients on Clozaril (27733) must have a CBC test performed at least every month, and failure to do so constitutes substandard care. The mechanism by which the strength parameter is determined is not central to this discussion; only that such a parameter is specified for purposes of the invention. In terms of rule definition, the strength parameter might be given as:

IF (MED)=[27733], THEN [FLAG][3]

In the foregoing, [FLAG] represents an output dimension, in this case a Diagnostic Test requirement, with a severity score of "3" which might indicate a mandatory test requirement.

Rule expressions, including strengths of association between dimensions, operate not only on individual dimensions, but also may be subsequently combined with entities that can exist within a dimension. For purposes of simplicity and ease of explanation, the following example assumes that each element symbol is represented by a unique numerical code, however derived or assigned. For example, suppose the condition of pregnancy=1234567 (PMEDHX dimension), the drug Accutane™=425372 (MED dimension), the drug Demerol=999111 (MED dimension), the drug phenelzine=220022 (MED dimension), removal of the spleen=555666 (PSURGHX dimension), folic acid=248612 (MED dimension), and that a vaccine against streptococcal pneumonia=987654 (MED dimension).

Given the foregoing, one might further assume that the following medical facts are known, compelling their compilation as "rules": Accutane causes severe birth defects in pregnancy and it is absolutely forbidden to use in a situation where the patient is, or is likely to become, pregnant. This rule implies that a combination of (MED dimension=Accutane)+ (PMEDHX dimension=pregnancy) would absolutely preclude prescribing Accutane in this patient. The rule would result in an output dimension of "absolute contraindication" if the input variables and arguments were as described.

Likewise, use of Demerol™ in a patient taking phenelzine can cause life-threatening seizures and therefore should never be administered. Again, this invokes a "rule" in which a combination of (MED dimension)+(MED dimension) returns an output dimension that absolutely precludes prescribing this combination for this patient, i.e., an absolute contraindication. Additionally, patients who have had their spleen removed should be vaccinated against streptococcal pneumonia because they are at high risk of meningitis, pneumonia, and death, and these are preventable by vaccination. In this case, the system according to the invention is able to evaluate a combination of the (PSURGHX dimension=spleen removal) and (MED dimension=pneumococcal vaccine) to determine that the patient has not been previously vaccinated and that a vaccination regimen is definitely indicated. The system returns an output dimension flag that looks for a vaccination (MED) parameter. If no vaccination has been entered, the system returns "vaccination desirable" to the user physician. This might be done in terms of a [VACCINATION] [SCORE] output dimension, where [SCORE] might refer to perhaps 1=desirable, and 2=mandatory.

In the following example, the severity score of association, for illustrative purposes, has been classified as mandatory due to the dangerous medical interactions described. In this scenario, input dimensions are given as:

Patient is pregnant=1234567
Patient is taking phenelzine=220022
Patient has had removal of the spleen=555666

These symbols are stored in the computer for any future use, and maintained unless changed (e.g., change of medicines, resolution of pregnancy). Some input variables will likely never change (e.g., removal of spleen is a historically permanent event, diseases like high blood pressure are incurable today and therefore are symptomatically managed only, but not cured, etc). On a future doctor visit, real time decision support could thus materialize in the following scenarios assuming that the doctor has recourse to the present invention.

The Patient visits the doctor for foot pain, and the doctor wishes to prescribe Demerol. When the MD tries to select Demerol=999111 in order to write the prescription, an appropriate rule, corresponding to (MED)=999111, is invoked, and an alert is immediately triggered and displayed, warning of possible seizures due to concurrent use of phenelzine. In another example, the Patient visits the doctor for acne, and the doctor wishes to prescribe Accutane, a treatment for Acne. When the MD tries to select Accutane=425372 in order to write the prescription, an alert is immediately triggered and displayed, warning of possible birth defects due to Accutane if the patient is pregnant. In this regard, the system will force a query for potential pregnancy if the demographic input for the patient is "F", i.e., female and the age parameter is between 15 and 55 (i.e., the patient is of child-bearing age).

As a further example, the Patient visits a family practice doctor for sore throat, and her OBGYN doctor has forgotten to start the patient on folic acid after diagnosing pregnancy 2 months ago. The system notes that the patient is pregnant (=1234567) but not taking folic acid (because the MED dimension=248612 is NOT present). A trigger is thus alerted, and the message "Folic acid is indicated in this patient because it reduces the incidence of childhood spinal deformity by 40%" is displayed. The Patient visits her OBGYN for a routine baby check up, and the doctor fails to realize the implications of her spleen being removed. An alert is immediately triggered and displayed, recommending vaccine against streptococcal pneumonia. It should be noted that these examples of context-specific decision support represent far-reaching value propositions beyond pure interaction checking. Furthermore, all rules can be invoked by machine symbolic reasoning, because all dimensions are included and a matched ontology exists for each term, as well as a metathesaurus of possible synonyms.

It will be clearly understood by one having skill in the art that the inventive framework above allows for the majority of clinical medical knowledge constraints to be simultaneously 'triangulated' to determine optimal therapeutic choices. For example, consider the interplay of numerous dimensions at once in the following scenario.

A pregnant female patient visits a doctor with a productive cough and the diagnosis of infectious bronchitis is made. The MD wishes to treat this patient with the best antibiotic. A query which would be automatically performed would associate relevant input dimensions with a relevant output (in this case, a drug therapy regimen). Based upon his experience, the CC dimension elements and any refinements developed in the context of a differential diagnosis, the MD determines bronchitis, and selects antibiotic choices as the output for the drug therapy request. The query is run automatically in the background by the system according to the invention in substantially the form shown below.

Show PREFERRED DRUG THERAPY in recommended
    order by SENSITIVITY (for likely causative organisms)
where INFECTION=BRONCHI and
where GEOGRAPHY=23411 (zip code)

In response to the above defined query, the system returns an initial result=Drugs A B C D E F G H I J (in this order). This initial result considers the fact that the treatment for infectious bronchitis is likely due to specific bacteria. The initial result must be further refined in accordance with the invention in order to take the various interactions into account. The system next:

Adjusts recommended therapies for:

| | |
|---|---|
| Co-existing medical problems | = LUPUS ERYTHEMATOSUS |
| | = GESTATIONAL DIABETES |
| Allergies | = MORPHINE, SULFA |
| Current medications | = INSULIN, PLAQUENIL |
| Co-existing medical conditions | = PREGNANCY | and finally returns an output=DRUGS OF CHOICE=C E F H J (in this exact order).

One should understand that multiple simultaneous processes have occurred. First, the initial list of drugs were determined according to the site of infection combined with the geographical area, as resistance to antibiotics varies according to location. Each of the factors are in accordance with "rules" that have been developed from the universal body of medical knowledge. Second, the initial order of medications was stratified according to sensitivity to likely causative organisms (stratified according to efficacy). Once this was determined, medications were excluded if known to be contraindicated (dangerous) in patients with specific coexisting diseases, co-existing allergies, co-existing medications, and co-existing conditions, i.e., excluded in accordance with developed "rules". From the physician's perspective, the entire process, and 'triangulation' of all inter-relationships was automatic and nearly effortless.

Most importantly, the physician is empowered to make optimal choices without actually possessing requisite and detailed medical knowledge. Moreover, optimal choices are not just based on safety (e.g., no bad interactions) but on therapeutic efficacy (e.g., best antibiotics for a given type of infection and geography, as shown in their preferred order) and cost (is the proposed medication covered by an insurance plan).

It should be noted that the decision support system's knowledge base can be continually updated, so that facts which are released as alerts (eg. an FDA recall), would be instantaneously indexed and delivered to the physician without delay were he seeing a patient in which the context were appropriate.

As a further example, one might consider the following illustrative scenario, where the object is to determine the preferred therapeutic options for treating a klebsiella-caused lower lobe pneumonia in a ventilator-dependent patient, also located in San Diego, Calif., and who has co-existing medical illnesses: systemic lupus erythematosus, atrial fibrillation of the heart, insulin-dependent diabetes, and hypertension. The patient is also allergic to morphine (which causes emesis) and all sulfa-class medications (which causes life-threatening anaphylaxis). The patient is currently taking insulin, cholorquine, nifedipine, melatonin, and the herbal supplement, St. John's Wort. His serum sodium is also decreased at 125 mmol/dL. Finally, within the spectrum of pharmacotherapy choices, the physician might wish the system to initially determine those drugs which are covered by the patient's health insurance plan.

Without recourse to the present invention, it is not possible, currently, to make this sort of determination in an automated fashion, and it may not be practicable to do so manually. Making this determination would involve manual searching through hundreds or even thousands of documents, each of which contains only a morsel of specific, yet highly-relevant information. The inability to do this with any degree of practical efficiency often results in a physician's having to rely on clinical guesswork without the benefit of full knowledge of the medical consequences of any decision. This "crap-shoot" nature of medical care is one of the principal causes of medical errors, which are known to kill or injure 770,000 persons per year in the U.S. alone, according to a U.S. Institute of Medicine report published in 1999. In effect, the "rules" by which this sort of determination may be made exist, but they exist in a highly disjoint form that is not susceptible to simultaneous combinatorial reasoning.

In the present invention, medical knowledge rules are structured into an XML-like definition in which data exists, for each dimension, in either a numeric, alphanumeric or symbolic architecture that enables machine reasoning. Machine reasoning thus enables massively fast, realtime, and patient-specific queries and can dramatically improve the quality of care. In the present example, a more complex query is exemplified, but the query process is indeed representative of common medical practice. In the example, one may assume that weighting elements can change dynamically and are able to be refined over time with experience. Specific elemental weighting is not therefore particularly germane to the present invention; but a methodology incorporating weighting is desirable. It should also be understood that the query process is described in terms of a sequence of steps or queries only as an aid to understanding. The actual process involves rule consultation and analysis which is more properly considered as parallel in nature. Thus the individual elements of the following query steps may be performed in any rational order and with respect to any rational ranking criteria.

First query=Retrieve antibiotics most likely to be effective against klebsiella-caused pneumonia based on known resistance patterns of this specific bacterium in the San Diego area (geographical variance in sensitivity to antibiotics is common and these factors are contained within the "rules").

Initial result=Drugs ABCDEFGHIJKLMNOPQRSTUVWXYZ (in this order) Assign efficacy weighting score (e.g., lowest rank=1, highest rank=26)

Second Query=check for dangerous interactions in a patient-specific fashion, and rank results (contraindication checking): Return a score for each based on severity of the interaction, eliminate absolute contraindicated drugs, and resort results. For example, interactions may be classified as suggesting "no contraindication", a "relative contraindication", or an "absolute contraindication", depending on the severity of the interaction. Interactions (taken from the "rules") might include:

Drug-Coexisting Medications Interactions
Drug-Coexisting Disease Interactions
Drug-Allergy Interactions
Drug-Lactation Interactions (if applicable)
Drug-Pregnancy Interactions (if applicable)
Drug-Non-Disease Clinical Condition Interactions (e.g., artificial ventilation, central venous catheter)
Drug-Genetic Status Interactions ((e.g., HLA B27)
Drug-Social History Interactions (e.g., 50 pack-year smoker)
Drug-Surgical History Interactions (e.g., recent 4 vessel heart bypass)

In all cases, the proposed medication list is adjusted to reflect a composite score based on composite of efficacy and interaction ranking, and thence reranked.

In the exemplary embodiment of FIG. 7, an initial listing of proposed medications has been reranked in terms of a number of significant considerations. In FIG. 7, medications are grouped into three major categories; No Contraindications, Relative Contraindications and Absolute Contraindications. Within each category, the medications may be arranged in order of therapeutic efficacy, cost per dose, existence on the formulary, or a combination of these factors. Necessarily, therapeutic efficacy will be a controlling parameter. Reranking might be done in accord with the following query parameters:

Third Query = Adjust Dosing of Medication based on
    Clinical Dimensions
    Co-existing disease adjusted clearance
    (e.g., kidney failure)
    Age-adjusted clearance Co-existing medications-adjusted clearance
    Genetic-adjusted clearance (e.g., cyt-P-450 mutation)
    Co-existing nondisease condition-adjusted clearance
    (e.g., ECHMO)
    Dose-adjust for efficacy based on nature and severity of disease
    (e.g., septicemia vs. pharyngitis)

| | |
|---|---|
| Fourth Query = | Economic considerations (Cost) |
| | Insurance Formulary Coverage |
| | Cost-benefit adjustment |

Adjust using Bayesian Analysis (i.e., what is probability that treatment will be effective given the patient has the disease?)

The final result of choices, as shown in FIG. 7=SCQEXZHBDFKQTM (in this order). In the final result, one should note that several of the initial choices have dropped down to the absolute contraindications category (they are highly dangerous to use in this patient). Additionally, some of the choices have been re-ordered due to weighting against relative contraindications. Further, certain of the choices (i.e., Q and E, indicated with underline characters) required dosage-adjustment for maximum safety and efficacy. For example, the "rule" might say that the use of drug E in the case of a diabetic (PMEDHX), requires dose modification to half the nominal dose. Similarly, the "rule" for drug Q might require one to prescribe half the nominal dose of drug Q in the case of a smoker (SOCFIX dimension).

Accordingly, the present invention can be understood as defining a particular system and methodology by which a drug therapy regimen may be defined for any particular patient in a manner that takes not only a drug's effectiveness into account, but also an entire universe of highly relevant clinical dimensions so as minimize the possibility of harmful interactions while simultaneously maximizing pharmacotherapy potential. Furthemore, as a consequence of its construction, in the present invention no rule can be overlooked by the reasoning system (unlike drug-drug or drug-allergy interaction checkers which are not comprehensive in all patient dimensions). The system and methodology utilizes a computerized dimensional indexing system implementing multiple databases and performs therapeutic determinations by symbolic structural reasoning with respect to database elemental indices.

In summary, the above unified data model simultaneously considers all important clinical dimensions using a symbolic representation of patient data combined with a symbolic representation of medical knowledge. The invention allows for automated inferencing by machine which can in real time present treatment choices that are simultaneously adjusted, in a patient and context-specific fashion, for interaction safety, therapeutic efficacy, economic factors, and correct dosing.

In terms of its systematic implementation, the present invention suitably comprises a set of relevant databases, hosted on a computer or data processing system of suitable type. The databases are accessible to a hand-held, laptop-type or desktop-type computer display for access by a physician or clinical worker. In addition to being hosted on a local data processing machine, the databases are contemplated as being maintained in a centralized data processing server implementation, such that it is accessible through a local or wide area network for download by a physician or practice group. Maintaining the database in a centralized location allows database terminology to be maintained on a more uniform basis, thereby minimizing the present-day confusion generated by inconsistent terminology for both indications and clinically relevant diagnoses. In a manner well understood by those having skill in the art, database contents are also uploadable to the centralized server so that additions and embellishments may be provided to the centralized system by physicians that may have discovered an additional indications usage for a particular medication and who wishes to share this information with the medical community at large.

In addition to being a self-contained medical decision support system, the system of the present invention also incorporates an interface to any one of a number of commercially or conventionally available electronic medical recordkeeping applications, such that as an exact diagnosis is extracted, the exact diagnosis is automatically ported to the appropriate input port of the medical records program. In particular, the data entry application, and its associated database, are implemented as an application software program that is written with the requisite I/O "hooks", such that it can be incorporated as an "applet" or "servelet" in a medical recordkeeping program. As patient information is added in conventional fashion, the medical record program invokes the application of the invention as soon as the physician reaches the "medications", "indications", or "diagnoses" portions of the recordkeeping program input.

Accordingly, the present invention can be understood as defining a particular system and methodology by which real-time, multidimensional medical decision support can be provided in a patient and context-specific fashion and in which critical information is delivered automatically and without substantial research effort by a user. While the above specification has shown, described and identified several novel features of the invention, as applied to various exemplary and illustrated embodiments, it will be understood that the embodiments are for purposes of illustration and ease of description only. Various omissions, substitutions and changes in the form and details of the exemplary embodiments may be made by those skilled in the art without departing from the scope and spirit of the present invention. Accordingly, the invention is not contemplated as being limited to the described, exemplary and illustrated embodiments, but are rather defined by the scope of the appended claims.

The invention claimed is:

1. A computerized method for providing multidimensional medical decision support, the method comprising:
    defining and storing, in a computer database, a set of input variables for a patient being evaluated, each input variable associated to a corresponding relevant clinical dimension for establishing a diagnosis for a patient, the relevant clinical dimensions are a chief complaint, a history of present illness, a past medical history, a past surgical history, a medication, an allergy, a vital sign, a physical exam (PE) and a diagnostic test;
    defining and storing, in the computer database, interdimensional relationships between and among the relevant clinical dimensions so as to define at least drug-disease, and drug-allergy testing interaction relationships;
    entering, into the computer, particular values for the input variables in the course of examining a patient;
    selecting at least a portion of the set of input variables from the group of relevant clinical dimensions consisting of a current complaint dimension, a medical history dimension, a surgical history dimension, a current medications dimension, a laboratory results dimension, a social history dimension, and a family history dimension;
    the computer automatically identifying particular ones of the interaction relationships specific to the particular patient being examined, wherein the particular ones of the interaction relationships are identified to a physician during the course of the examination;
    displaying the particular ones of the interaction relationships specific to the particular patient during the examination of the patient by the physician; and the computer automatically inferences in real time and presents treatment choices that are simultaneously adjusted, in a patient and context-specific fashion, for interaction safety, therapeutic efficacy, economic factors, and correct dosing.

2. The method according to claim 1, further comprising:
selecting at least an additional portion of the set of input variables from the group of relevant clinical dimensions consisting of a diagnostic test findings dimension, a vital signs dimension, a physical examination findings dimension, and a diagnostic possibility dimension.

3. The method according to claim 2, further comprising:
topologically mapping the inter-relationships between and among the relevant clinical dimensions; and
assigning a severity score to each mapped association between and among the clinical dimensions so as to define a strength of each mapped association.

4. The method according to claim 3, further comprising:
defining a set of output variables for a patient being evaluated, each output variable associated to a corresponding relevant intervention action for establishing a treatment regime for a patient; and
wherein the interaction relationships identified to the physician automatically inform an intervention action in accordance with the existence and strength of a mapped association between clinical dimensions.

5. The method according to claim 4, wherein the relevant intervention actions are selected from the group consisting of counseling, pharmacotherapy, procedural intervention, diagnostic testing, and specialist referral.

6. The method according to claim 5, wherein the chief complaint dimension defines a differential diagnosis selected from a recognized standardized medical reference of clinically relevant diagnoses.

7. The method according to claim 6, wherein the recognized standardized medical reference comprises the ICD9.

8. The method according to claim 7, wherein ICD9 or equivalent disease codes are automatically entered into an electronic patient medical record.

\* \* \* \* \*